United States Patent
Stipanovic et al.

(10) Patent No.: US 6,919,021 B2
(45) Date of Patent: Jul. 19, 2005

(54) SIMULATED ACTIVITY OF PROTEIN A DISPLAYED BY LIGANDS ATTACHED TO A CELLULOSE BEAD SURFACE

(75) Inventors: Bozidar Stipanovic, Lake Forest, IL (US); Martin Griffin, Skokie, IL (US); Ioannis Scarpa, Chicago, IL (US)

(73) Assignee: Accurate Polymers, Ltd., Highland Park, IL (US)

( * ) Notice: Subject to any disclaimer, the term of this patent is extended or adjusted under 35 U.S.C. 154(b) by 272 days.

(21) Appl. No.: 10/410,531

(22) Filed: Apr. 8, 2003

(65) Prior Publication Data

US 2003/0209491 A1 Nov. 13, 2003

Related U.S. Application Data

(62) Division of application No. 09/846,471, filed on Apr. 30, 2001, now Pat. No. 6,572,767.
(60) Provisional application No. 60/200,591, filed on Apr. 28, 2000.

(51) Int. Cl.[7] .............................................. B01D 15/08
(52) U.S. Cl. ................................ 210/198.2; 210/502.1; 210/635; 210/656; 502/404; 502/439
(58) Field of Search ................................. 210/635, 656, 210/659, 198.2, 502.1; 502/401, 404, 439

(56) References Cited

U.S. PATENT DOCUMENTS

| | | |
|---|---|---|
| 5,240,602 A | 8/1993 | Hammen ................. 210/198.2 |
| 5,942,463 A | 8/1999 | Oscarsson et al. ....... 210/502.1 |
| 6,315,900 B1 * | 11/2001 | Stipanovic et al. ...... 210/198.2 |

FOREIGN PATENT DOCUMENTS

| | | | |
|---|---|---|---|
| WO | WO 91/03257 | 3/1991 | .............. 210/198.2 |
| WO | WO 97/10887 | 3/1997 | .............. 210/198.2 |

OTHER PUBLICATIONS

Schwarz, Alexander, *Five-membered Mercaptoheterocyclic Ligands for Thiophilic Adsorption Chromatography*, J. Molecular Recognition 9: 672–674, 1996.

Li, Rongxiu, Victor Dowd, David J. Stewart, Stephen J. Burton, and Christopher R. Lowe, *Design, synthesis, and application of a Protein A mimetic*, Nature Biotechnology 16: 190–195, 1998.

Fassina, Giorgio, Antonio Verdoliva, Maria Risaria Odierna, Menotti Ruvo and Giovanni Cassini, *Protein A mimetic Peptide Ligand for Affinity Purification of Antiobiotics*, Journal of Molecular Recognition 9: 564–569, 1996.

* cited by examiner

*Primary Examiner*—Ernest G. Therkorn
(74) *Attorney, Agent, or Firm*—Fitch, Even, Tabin & Flannery

(57) ABSTRACT

A method and compound for the purification of proteins including the attachment of a non-peptidic, small compound which simulates the affinity of Protein A for immumoglobulins to a support matrix. Once attached on the support matrix, the resulting monochloro-triazine derivative is reacted with an excess of an amino compound at a higher temperature to achieve high levels of substitution. The resulting support matrix with ligand is useful in the affinity separations of antibodies. Further, a mercapto heterocyclic system ligand may be attached to the super matrix and useful in affinity separations of antibodies.

9 Claims, No Drawings

SIMULATED ACTIVITY OF PROTEIN A DISPLAYED BY LIGANDS ATTACHED TO A CELLULOSE BEAD SURFACE

RELATED APPLICATION

This application is a divisional application under 37 C.F.R 1.53(b)(1) of prior application Ser. No. 09/846,471, filed on Apr. 30, 2001, now U.S. Pat. No. 6,572,767, entitled SIMULATED ACTIVITY OF PROTEIN A DISPLAYED BY LIGANDS ATTACHED TO A CELLULOSE BEAD SURFACE, which claims the benefit of the filing date under 35 U.S.C. §119(e) to provisional U.S. Patent Ser. No. 60/200,591 filed on Apr. 28, 2000 both of which are hereby incorporated by reference.

BACKGROUND OF THE INVENTION

All current protein purification systems show deficiencies, especially for large-scale purifications. In particular, the purification of antibodies is inadequate as far as purity and yields are concerned. Consequently, the present state of the art processes are costly due to large volumes of solvents and long production times for making pure immunoglobulins intended for therapeutic and diagnostic applications.

In an affinity separation, the protein being purified adsorbs selectively and reversibly to a complimentary binding substance or affinity ligand, often times an antibody molecule. Affinity separation generally results in very low non-specific binding compared to other separation techniques. The very low non-specific binding makes it possible to purify a given protein from complex biological mixtures, to separate incorrectly folded forms from native molecules, and to recover the protein.

Purification systems using glass or metal tubes that contain a packed column of separation medium, for example, beads or particles, are known. These tubes are known as column boxes. Because the separation medium is compacted within the column boxes, the flow rates are slow and the column boxes have a limited capacity. Therefore, prior art purification technology has focused on increasing the porosity of the separation medium to increase the flow rates and capacity within the column box. The object of these known systems is to purify the largest amount of material within the shortest amount of time while keeping the amount of contaminants in the product low and the product yields high. One problem with the old purification technology is that increasing porosity of the separation medium achieved faster flow rates and capacity, but reduced product yields and purity.

Orbicell™ cellulose beads are available from Accurate Polymers, Ltd. in Illinois and described in U.S. Pat. No. 6,315,900 issued on Nov. 1, 2001 to Stipanovic et al. entitled Static Separation Method Using Non-Porous Cellulose Beads, incorporated herein by reference.

A typical affinity adsorbent consists of a solid support, a spacer arm, and a ligand. The spacer arm may encourage protein binding by making the ligand more accessible. Certain affinity separation products do not have a spacer arm of sufficient length or suitable nature so as to aid in the attachment of the target compound, for example, an antibody. In order to overcome this limitation, there is a need for a spacer arm that would allow for better orientation of the ligand, decreased steric hindrance between the target compounds, and decreased steric hindrance between the ligands thereby allowing for greater attachment of the target compound. Ease in attachment of the target compound to the ligand due to the geometry of the spacer arm and/or ligand increases target compound yield. There is a need in the art for the ligand to exhibit specific and reversible binding to the target compound, for example, a protein such as an antibody.

Affinity chromatography on immobilized Staphylococcus Aureus Protein A (SpA), Protein G and Protein M columns is a recent purification method for monoclonal and polyclonal antibody production. These bacteria-derived proteins are not only costly to produce, but also suffer from biological and chemical instability. An ability to be cleaned and sterilized is an absolute requirement by regulatory authorities for sorbents used to purify antibodies destined for therapeutic end use. Polyclonal antibodies, as well as more recently developed monoclonals, are routinely purified by affinity column chromatography. These antibodies have wide applications in the diagnostic field, but lately similar antibodies are more and more finding their use in therapeutic applications. The latter application can hardly tolerate any instability of affinity sorbents, which becomes especially critical when steam, or harsh chemical sterilization procedures are mandated by regulatory agencies.

Of course, the therapeutic end-use will create a demand for much larger quantities of highly purified antibodies than the diagnostic field ever did. The first obstacle that the present state of the art-technology faces on any future scale-ups is the high cost of these bacteria-derived proteins. On top of the high cost of sorbents will be the regulatory authorities thorough scrutiny of potential instabilities of sorbents during the required sterilization protocols. Therefore, there is a need in the art to solve these and other difficulties of the prior art.

Recent advances in molecular modeling have enabled research groups to come up with much smaller molecules than bacteria-derived proteins, which surprisingly, can still simulate high affinity and selectivity of respective bacterial proteins for numerous immunoglobulins. Said model synthetic compounds possessing affinity for antibodies range from simple monocyclic and polycyclic compounds to peptides of short to medium length. Some of these peptides are linear while others have macrocyclic structure.

BRIEF SUMMARY OF THE INVENTION

The present invention is directed to novel ligands, a method of preparing the ligands, a method of using the ligands in the purification of compounds, and the attachment of the novel ligands to cellulose beads.

The large-scale purification of bio-molecules and, in particular, immunoglobulines, is accomplished by using a cellulose bead attached to small, non-peptidic compounds which display a high affinity and selectivity for the bio-molecule to be purified. In addition, the beads with the attached ligands of Formulas I–IV also possess a high chemical stability under rigors of recycling and sterilization. A method of purifying a compound includes providing a support matrix having a ligand of Formula I–IV thereon to a solution containing a compound to be separated, allowing for interaction of the ligand and compound to be separated, and washing the support matrix to elute the compound to be separated. In one embodiment, the support matrix may include a spacer.

The invention will best be understood by reference to the following detailed description of the preferred embodiment, taken in conjunction with the accompanying drawings. The discussion below is descriptive, illustrative and exemplary and is not to be taken as limiting the scope defined by any appended claims.

DETAILED DESCRIPTION OF THE INVENTION

In one embodiment, Formula I shows a non-peptidic, small compound that simulates the affinity of Protein A for immunoglobulins. A compound which simulates the affinity of Protein A can also be referred to as a protein A mimetic (PAM). As shown in Reaction 1, ligands of Formula I can be prepared and immobilized on Orbicell™ beads having a spacer surface chemistry terminated with an amino group on a linear polyethylene glycol molecule of molecular weight ranging between 64 and 2000 daltons. Hydrazine can be reacted with the terminal esters resulting in a molecular super-structure which is terminated with hydrazide functionalities (a). In a further embodiment, the molecular super-structure has a terminal functional group selected from the group consisting of succinimidyl, thiophenyl, 2,4-dimethoxy-s-triaznyl, cynomethyl, chloroformyl, and para-nitrophenyl esters. The cellulose beads can range in size from about 0.1 microns to 20 microns. The molecular super-structure improves the geometry of the resulting attached ligands. The two terminal hydrazine groups of the molecular super-structure allow for a plurality of ligands to attach.

In one preferred embodiment, the immunoglobin to be separated is IgG. A hydrophobic interaction occurs between the IgG molecule and a mimetic SpA ligand attached to a support matrix, such as Orbicell™ beads. In this manner, the IgG is separated from the solution to which are added the non-porous, cellulose beads with the attached mimetic SpA ligands. The IgG attaches to the mimetic SpA on the beads. The beads with the resulting ligand-IgG complex are washed of impurities so that a subsequent elution results in IgG and reusable beads having a regenerated ligand for repeated binding with IgG. The present ligand more easily attaches to the support matrix and has a greater reactivity with the IgG.

As shown in Reaction 1, once terminated with hydrazide functionalities, an s-triazinyl moiety (b) can be attached. The reaction with the hydrazine was achieved at the dichloro-s-triazine stage, as the second chloride is of much higher reactivity than the third chloride. Since all of the chlorides are not reacted, the compound is highly reactive and high reactivity increases yield. Once attached on the bead surface, the resulting monochloro triazine derivative (c) was forced to react with an excess of an amino compound (d) at a higher reaction temperature than used in other stages of the reaction.

The present ligand of Formula I is attached to the solid state complex (the support matrix or, for example, the Orbicell™ bead) under better spatial control and has a greater reactivity with the IgG (or other target compound to be purified). At least these factors increase the total yield of the purified IgG. The hydrazine moiety on the cellulose surface reacts readily with the very reactive chloride of dichlorotriazine molecule. The desired molecular geometry of two adjacent ligand groups should result in multiple points of attachment of the IgG to the ligands. The hydrazine represents the shortest bifunctional $NH_2$ group linker which allows optimal spatial arrangement and proximity of the ligands. Therefore, the addition of the improved ligand with the improved spatial arrangement on the surface, in conjunction with improved non-porous Orbicell™ bead, increases the interaction between the matrix and the IgG (i.e., other antibody or target compound).

Reaction 1

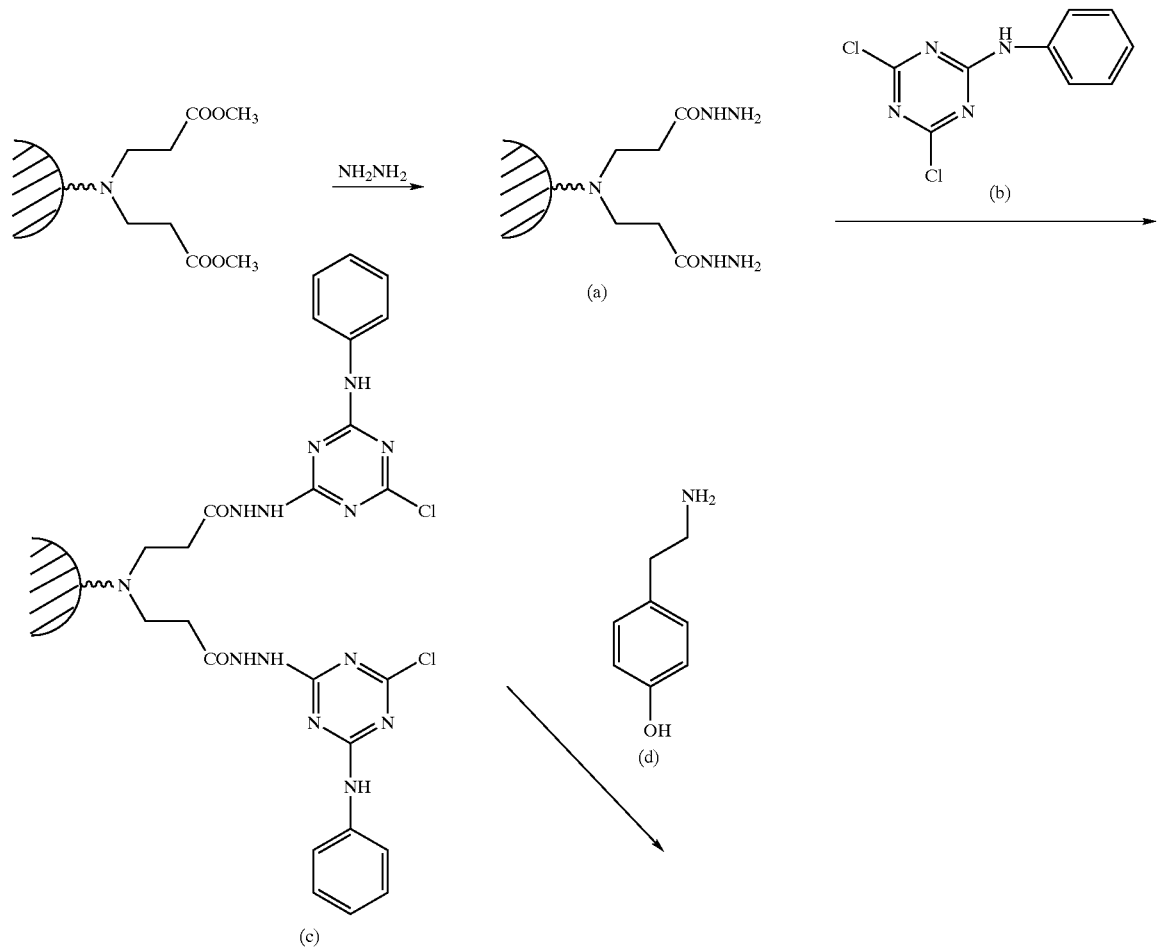

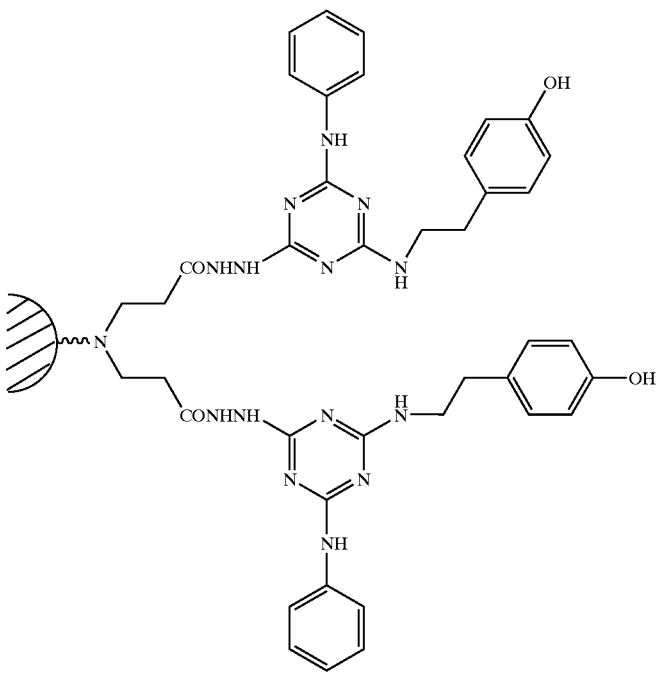

Formula I

Very high levels of substitution of the monochloro triazine derivative were achieved. The ligand of Formula I was tested for affinity separation of antibodies. The sorbent displayed very high activity (yield of antibody was 44 mg/g of beads) and selectivity (pure antibodies by HPLC: no "shoulders" of impurities present).

In another embodiment, an alternative ligand that simulates Protein A activity toward immunoglobulin is derived from a meta phthalic acid derivative. As shown in Reaction 2, a molar excess of dimethyl-5-nitroisophthalate is reacted with tiramine in methanol and monoamide is isolated and crystallized (a). 5-Nitro monoamide of isophthalic acid ester is further reacted with excess of aniline, providing mixed 5-nitro bisamide (b). Hydrogenation over Pd catalyst under $H_2$ pressure gives mixed 5-amino bisamide compound (c), SA-B.

Reaction 2

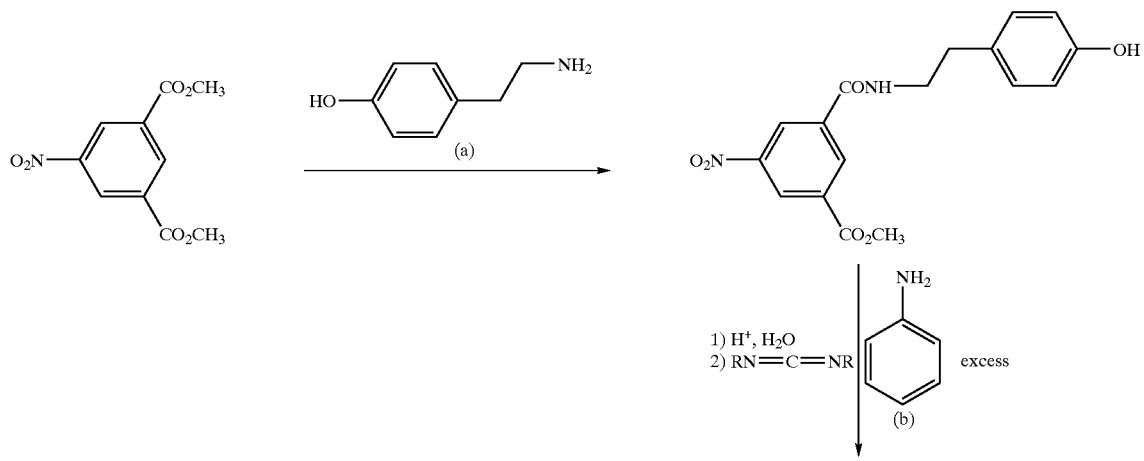

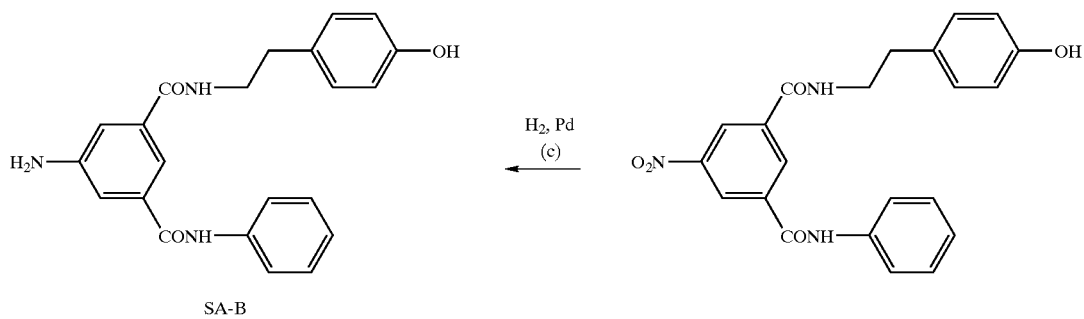

SA-B

Compound SA-B can now be grafted onto the surface of cellulose beads having a spacer arm that is carboxyl functionalized activated via N-succinimidyl ester, as shown, resulting in ligand of general Formula II.

In another embodiment, a method of manufacturing a ligand of Formula II includes reacting a (4' hydroxy) phenetyalmido-1-carboxy-anilido-3-carboxyphenyl-5-amine with a terminal, activated ester functional group.

Reaction 3

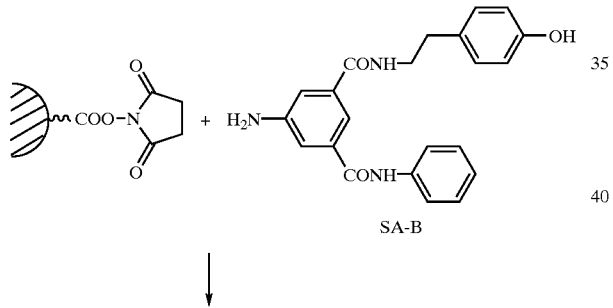

SA-B

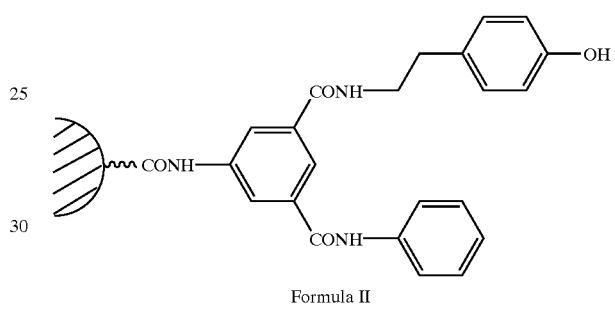

Formula II

In another embodiment, a method of manufacturing a ligand of Formula III includes reacting a (4' hydroxy) phenetyalmido-1-carboxy-anilido-3-carboxyphenyl-5-amine with a terminal tertiary dicarboxy-ethyl amine in the presence of a peptide-coupling agent.

Another alternative grafting method is based on coupling of carboxyl-functionalized beads with amino SA-B using a conventional carbodimide reagent, as shown in Reaction 4, resulting in the ligand of general Formula III shown below.

Reaction 4

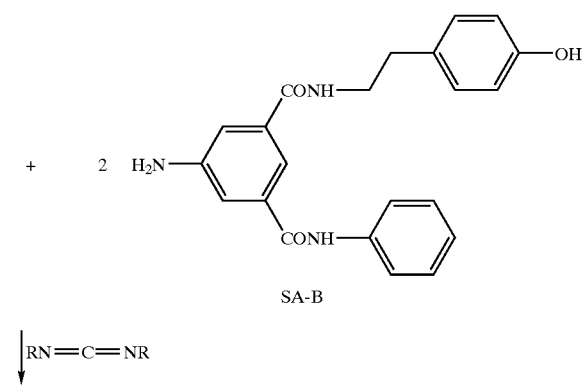

SA-B $RN=C=NR$

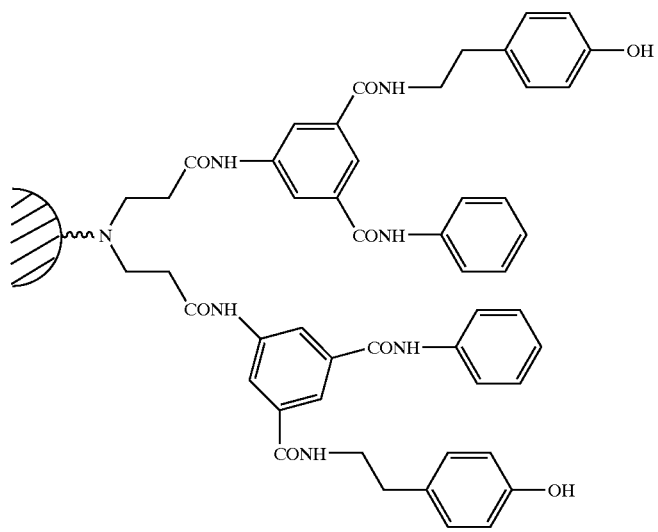

Formula III

A further embodiment of the adsorbents include a non-porous cellulose bead having a diameter of approximately 0.1 to 20μ being pegylated on the surface with α,ω-diamino polyethylene glycol groups ranging in molecular weights up to approximately 60 to 2000 Daltons. The primary amines are reacted with a triepoxide to form an amino-2-hydroxy adduct. The remaining epoxides are reacted with the thiol (mercapto) heterocyclic compounds wherein the R group includes pi electron rich systems resulting in the ligands of general Formula IV. The mercapto heterocyclic compounds may be selected from the group comprising mercapto-N-methyl imidiazol, 2-mercapto pyridine, mercaptopyridine-N oxide, 2-mercaptoimidazole, 2-mercaptobenzimidazole, sodium 2-mercapto-5-benz-imidazolesulfonic acid, 2-mercapto-benzothiazole, 2-mercaptobenzoxazole, 2-mercapto-5-methylbenzimidazole, 2-mercapto-1-methylimidazole, 2-mercapto-4-methylpyrimidine, 2-mercapto-5-nitrobenzimidazole, 2-mercaptopyridine, 2-mercaptopyridine N-oxide, 2-mercapto-pyrimidine, 2-mercapto-4(3H)-quinalozine, 2-mercaptothiazoline, 2-mercapto-thiazole, 2-mercaptothiadiazole, and 5-methyl-1,3,4-thiadiazole-2-thiol and other mercapto heterocyclic compounds known to those skilled in the art. The grafted mercapto heterocyclic compounds selectively bind to biological molecules, including IgM, IgY (egg), Fab, and Fc antibody fragments in addition to the whole IgG molecule.

Reaction 5

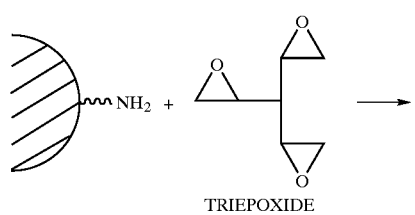

TRIEPOXIDE

-continued

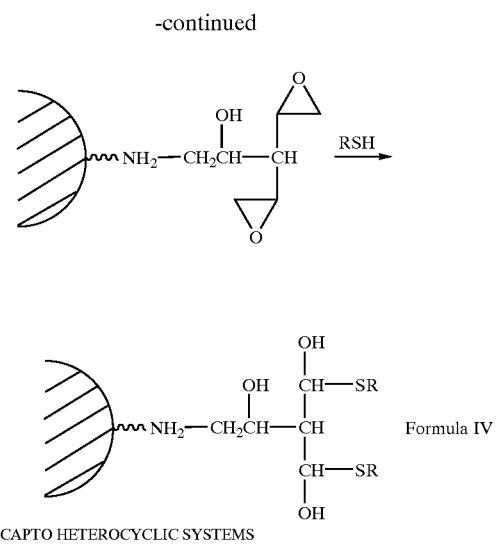

Formula IV

RSH = MERCAPTO HETEROCYCLIC SYSTEMS

One skilled in the art could accomplish substitution of the phenol groups of Formulas I–IV with a thiol, amide or other equivalents. Additionally, salts of Formulas I–IV are included.

In one embodiment, the method of purification includes providing a mimetic Protein A (SpA) capable of binding immunoglobin. The mimetic Protein A is attached to a support matrix. In a preferred embodiment, the support matrix is a cellulose bead. In a preferred embodiment, the immunoglobin to be separated is IgG. An intereaction occurs between the IgG molecule and the mimetic SpA ligand. The beads with the resulting ligand-IgG complex are washed of impurities so that a subsequent elution results in pure IgG and reusable beads having a regenerated ligand for repeated binding with IgG.

EXAMPLE 1

In the protein purification method of Example 1, 200 grams of amino functionalized Orbicell™ beads are placed in 2 liters of propanol under vacuum with mild heat. The great majority of all water was removed through the distillation of approximately 200 ml of azeotrope. To the suspension in propanol, approximately 100 g of methyl acrylate was added and the resulting suspension heated in a water bath at approximately 68° C. for about 36 hours while rotated or stirred and allowed to react. After the reaction is complete, as indicated by a negative test for amino group on the Orbicell™ beads, the suspension is left stirring until cooled to about 35° C. After cooling, the reaction mixture is roto-evaporated, distilling off about 1000 to 1200 ml of azeotrope (5% methyl acrylate-95% n-propanol). During distillation, another portion of 1L of n-propanol is added to the distillation and continued until the total volume of azeotrope distillate reached 2.1 to 2.2 liters. At this time the suspension retained only a faint odor of methyl acrylate.

EXAMPLE 2

The total volume of the suspension obtained in Example 1 was adjusted with n-propanol to a total volume range of 1100 to 1200 ml. With vigorous mixing, 70 grams anhydrous hydrazine was added and the suspension was stirred for about 14–16 hours at approximately 45° C. The resulting reaction product was centrifuged and the hydrazide beads were washed three times with propanol. After the propanol wash, the beads were washed exhaustively with water until the filtrate tested negative for hydrazine.

EXAMPLE 3

The wet hydrazide-functionalized beads from Example 2 containing about 100 g of dry beads were dispersed in 400 ml of 0.1 molar sodium diacetate (5.7 g of commercial sodium diacetate, crystalline, in 395 ml of distilled water). To this aqueous suspension was added a solution of 1000 ml of dimethoxyethane and 53 g (0.22 moles) of anilino-dichloro-s-triazine. The suspension was stirred for about 6 to 8 hours at 45° C. After testing negative for hydrazide, the beads were isolated by centrifugation and washed once with dimethoxyethane. The beads were then washed five times with ethanol followed by one washing with N-methylpyrrolidone.

EXAMPLE 4

The beads from Example 3 were dispersed in 1 liter of N-methylpyrrolidone and 25 g of tiramine (0.2 moles) were added. The reaction mixture was heated to and maintained at 68° C. for about 36 hours with stirring. After cooling to room temperature, the beads were washed three times with N-methylpyrrolidone and three times with n-propanol on the basket centrifuge. Exhaustive washing with water in a tangential flow system yielded the ligand of Formula I.

EXAMPLE 5

Approximately 23.27 grams of 3–7$\mu$ Orbicell™ beads having an primary or secondary amino group thereon were washed 6 times with 98% ethanol. The suspension was placed in 200 ml of ethanol to which 7.8 grams of triepoxide is added and the mixture stirred at about 64° C. for about 18 hours. A 2,4,6-trinitrobenzenesulphonic acid (TNBS) test showed complete reaction of the amines on the beads. The mixture was washed on a benchtop centrifuge with ethanol, followed by water, and finally 0.15 M sodium carbonate at a pH of 9.7 and suspended in a 100 ml of a mixture comprising 65 ml of ethanol and 35 ml of 0.15 M sodium carbonate buffer at pH of 9.5. To this suspension about 2.7 grams of thioimidazol was added and the suspension was stirred for about 18 hours at room temperature. The suspension was then washed with water. Without the need for further cleaning, the beads having a ligand of Formula IV can be used in binding experiments.

EXAMPLE 6

Isolation of Egg Yolk IgY Using Orbicell™ Simul-M Bead

A commercial egg yolk was extracted with 150 ml of 0.05M phosphate buffer at a pH 8 and was delipidized by shaking with polystyrene beads. The extract was adjusted to 0.5 M $Na_2SO_4$ by the addition of the solid salt. Orbicell™ beads with the ligand of Formula IV were added and the suspension was shaken/stirred for 1 hour. The suspension was introduced into a separation apparatus (e.g. TAPS or a crossflow system on a benchtop basket centrifuge) and the beads washed with 0.5 M $Na_2SO_4$. IgY is eluted from the washed beads with 0.01 M sodium phosphate, pH 7.5. The purified IgY is checked for purity by SDS/polyacrylamide gel electrophoresis (PAGE) and/or HPLC. The results of the above purification are represented in Table 1.

TABLE 1

PURIFICATION OF EGG YOKE IgY

| STEP | AMOUNT IgY PER EGG | % PURITY |
| --- | --- | --- |
| Delipidized Egg Yoke | 100 mg | 15 |
| Ammonium Sulfate Precipitation | >70 mg | 70–80 |
| Simul-M Affinity | >60 mg | >90 |

EXAMPLE 7

Use of Several Methods of Separating Solutions from Orbicell™ Affinity Beads

Commercial human Immunoglobulin G (all classes) [hIgG], 2.00 mg, was dissolved in 1.5 ml of 150 mM NaCl in 10 mM $NaHPO_4$, pH 7.5 (pBS). To this solution was added 0.125 ml of moist Orbicell™ beads grafted with Formula I (equivalent to 25 mg of dry beads) and the beads suspended by vortex mixing. The suspension was then rocked gently on a platform rocking-shaker. After about 1 hour the beads were centrifuged into a pellet (moderate speed on a microfuge) and the supernatant removed and read on a spectrophotometer at 280 nm. The decrease of optical density at 280 nm ($OD_{280}$) showed that more than 85% of the IgG was bound to the beads. The beads were then washed five (5) times with pBS by suspension in pBS centrifugation, decanted, resuspended in pBS and recentrifuged. The $OD_{280}$ of the washes decreased to blank values by the fourth or fifth wash, indication of little or no unbound IgG. The beads were suspended in 0.2 M glycine HCl, pH 2.5 (1.5 ml) and recentrifuged. The separated supernate containing the IgG was neutralized with 2 M Tris Cl, pH 8. This extraction was repeated twice to furnish greater than 90% of the IgG (1.8 mg).

The centrifugation method was employed successfully, for other immunogloblin containing solutions. For instance, commercial IgA was added to a corn endosperm extract (a prototype purification for immunogloblins-secreting, genetically engineered corn). Adding beads grafted with Formula I-type affinity beads followed by the incubation (23±2° C.), followed by centrifugation, decantation, washing with pBS (five times), followed by extraction of the bead-bound IgA furnished a yield of about 97% from starting IgA. Analytical PAGE of a dissociated IgA sample showed the three bands characteristic of starting material with only trace amounts of corn-extracted proteins.

Besides cross-flow and direct centrifugation (to obtain a pelleted mass) other methods of separation solutions (or water) from Orbicell™ beads include: basket centrifugation (the liquid passes through the bead mass and a woven basket filter); moving, porous belt separation (the liquid passes through the belt), continuous centrifugation, moving mass perfusion of liquid past the beads, and many others.

EXAMPLE 8

Into a 400 ml sample of a CHO cell perfusate containing 40 µg/ml of monoclonal IgG antibody (MoAb) and about 20 µg of contaminants were added 600 mg of dry Orbicell™ beads grafted the ligand of Formula I. The suspension was agitated gently for approximately one and a half hours at room temperature (approximately 28° C.) until the absorption of the MoAb was complete. The suspension was concentrated on a cross flow micro filtration system down to 60 ml (about a 1% suspension). The beads were then washed of contaminants with 10 volumes (600 ml) of 50 molar phosphate buffer with 200 mmoles/liter of NaCl at a pH of 7.5 (slightly base). The adsorbed antibody was eluted with 10 volumes (600 ml) of 0.2 molar glycine hydrochloride buffer at an approximate pH of 2.5 and immediately neutralized by introducing the permeate from the filter into a molar tris-buffer solution of approximate pH of 8.5. The neutralized MoAb solution was concentrated by ultrafiltration (50,000 molecular weight cut-off membrane) and characterized by polyacrylamide gel electrophoresis (PAGE) of a sodium dodeyl sulfate/mercaptoethanol dissociated samples. Also, high pressure ligand chromatography (HPLC) (size-exclusion type) was also used for some sample characterizations and quantitation. The MoAb was about 96% pure by HPLC and the approximate yield was 92%.

No license is expressly or implicitly granted to any patent or patent applications referred to or incorporated herein. As noted, the discussion above is descriptive, illustrative and exemplary and is not to be taken as limiting the scope defined by any appended claims.

We claim:

1. A purification compound comprising:

a support matrix; and a ligand of Formula IV.

2. The purification compound of claim 1 wherein the support matrix is a cellulose bead.

3. The purification compound of claim 2 wherein the cellulose bead is substantially non-porous.

4. The purification compound of claim 3 wherein the cellulose beads range in size from about 0.1 microns to 20 microns.

5. The purification compound of claim 1 further comprising a spacer arm linking the cellulose bead with the ligand of Formula IV.

6. The purification compound of claim 5 wherein the spacer arm is a linear polyethylene glycol molecule of molecular weight ranging between about 64 and 2000 daltons.

7. The purification compound of claim 5, further comprising a molecular super structure, wherein the molecular super-structure is a terminal, reactive epoxy functional group linked to the spacer arm.

8. A method of manufacture of a ligand of Formula IV comprising:

reacting a primary amino group on a spacer arm with a triepoxy compound to form a terminal diepoxy compound; and reacting the terminal diepoxy compound with a mercaptoheterocyclic compound.

9. The method of manufacture of claim 8 wherein the mercaptoheterocyclic compound is selected from the group consisting of mercapto-N-methyl imidiazol, 2-mercapto pyridine, mercaptopyridine-N oxide, 2-mercaptoimidazole, 2-mercaptobenzimidazole, sodium 2-mercapto-5-benzimidazolesulfonic acid, 2-mercapto-benzothiazole, 2-mercaptobenzoxazole, 2-mercapto-5-methylbenzimidazole, 2-mercapto-1-methylimidazole, 2-mercapto-4-methylpyrimidine, 2-mercapto-5-nitrobenzimidazole, 2-mercaptopyridine, 2-mercaptopyridine N-oxide, 2-mercapto-pyrimidine, 2-mercapto-4(3H)-quinalo-zine, 2-mercaptothiazoline, 2-mercapto-thiazole, 2-mercaptothiadiazole, and 5-methyl-1,3,4-thiadiazole-2-thiol and combinations thereof.

* * * * *